(12) United States Patent
Parker et al.

(10) Patent No.: US 7,297,807 B1
(45) Date of Patent: Nov. 20, 2007

(54) INTERMEDIATES FOR THE SYNTHESIS OF POLYPROPIONATE ANTIBIOTICS

(75) Inventors: Kathlyn Parker, Setauket, NY (US); Huanyan Cao, New York, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/421,290

(22) Filed: May 31, 2006

(51) Int. Cl.
*C07F 7/02* (2006.01)

(52) U.S. Cl. .................. 556/400; 568/8; 568/300; 568/579; 568/700; 546/6; 546/257; 548/400; 548/407; 548/413; 549/5

(58) Field of Classification Search ............... 556/400; 568/8, 300, 700, 579; 546/257, 6; 548/400, 548/407, 413; 549/5
See application file for complete search history.

(56) References Cited

FOREIGN PATENT DOCUMENTS

WO WO 2002/057251 7/2002

OTHER PUBLICATIONS

Hung et al., {Syntheses of Discodermolides Useful for Investigating Microtubule Binding and Stabilization, Journal of the American Chemical Society (1996), 118(45), 11054-11080}.*
Tsai, et al., "Acyclic stereocontrol through diastereo- and enantioselective [2,3]-sigmatropic Witting rearrangements," *J. Org. Chem.*; 1984, 49(10):1842-1843.
Parker, et al., "Scalable, Catalytic Asymmetric Synthesis of Syn, Anti Stereotriad Building Blocks for Discodermolide," *Organic Letters* 2006, 8(16):3541-3544.
Ziegler, et al., "Applications sof the 3-Methyl-γ-butyrolactone Strategy to the Synthesis of Polypropionates: The Prelog-Djerassi Lactonic Ester, *ent*-Invictolide, and the $C_{19}$-$C_{27}$ Fragment of Rifamycin $S^1$," *J. Am. Chem. Soc.* 1988, 110(16):5442-5452.
Freemantle, Michael, "Scaled-up Synthesis of Discodermolide," http://www.CEN-ONLINE.org, Mar. 1, 2004.

Shahid, et al., "A straightforward, highly stereoselective construction of eight stereogenic centers in (+)-discodermolide C1-C13 segment, based on a strategy of iterative aldol reactions," *Tetrahedron Letters* 2002, 43:6377-6381.
Choy, et al., "Simplidied Discodermolide Analogues: Synthesis and Biological Evaluation of 4-epi-7Dehydroxy-14,16-didemethyl-(+)-discodermolides as Microtubule-Stabilizing Agents," *J. Med. Chem.* 2003, 46:2846-2864.
Smith, et al., "Gram-Scale Synthesis of (+)-Discodermolide," *Organic Letters* 1999, 1(11):1823-1826.
Karisalmi, et al., "Stereoselective synthesis of the C9-C19 lactone-dipropionate fragment of calyculin C," *Tetrahedron Letters* 2004, 45:1-4.
Parker, et al., "A Strategy for Exploiting the Pseudosymmetry of the C1-C13 Stretch of Discodermolide," *Organic Letters* 2004, 6(9):1413-1416.
Smith, et al., "A Practical Improvement, Enhancing the Large-Scale Synthesis of (+)-Discodermolide: A Third-Generation Approach," *Org. Lett.* 2003, 5(23):4405-4408.
Tsai, et al., Application of [2,3] Sigmatripic (wittig) . . . *J. AmChem Soc* 1985, 107:3915-3918.

* cited by examiner

*Primary Examiner*—Johann Richter
*Assistant Examiner*—Chukwuma Nwaonicha
(74) *Attorney, Agent, or Firm*—Hoffmann & Baron, LLP

(57) ABSTRACT

The invention relates to intermediate compounds of the formula

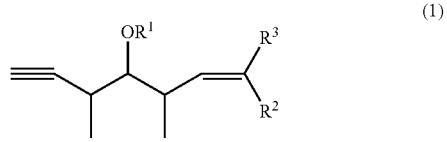

(1)

wherein $R^1$ is H or a protecting group, $R^2$ and $R^3$ each independently represent H, methyl, or a leaving group, provided that at least one, but not both, of $R^2$ and $R^3$ is a leaving group. The intermediate compounds are useful for the synthesis of discodermolide, its derivatives, and related compounds.

27 Claims, No Drawings

INTERMEDIATES FOR THE SYNTHESIS OF POLYPROPIONATE ANTIBIOTICS

The present invention was made in part with government support under Grant No. 5R01CA87503 awarded by the National Institutes of Health. The United States government has certain rights in this invention.

BACKGROUND OF THE INVENTION

Discodermolide, more specifically referred to as (+)-discodermolide, is a microtubule-stabilizing drug which is found naturally in the Caribbean sponge *Discodermia dissolute*. Discodermolide has attracted widespread attention because of its known potent inhibition of tumor cell growth. The structure of discodermolide is shown below:

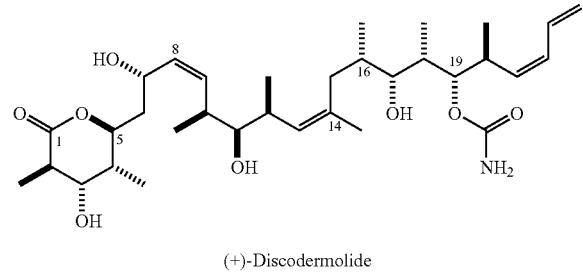

(+)-Discodermolide

As evidenced by the structure above, discodermolide is a structurally complex molecule. Contributing to its complexity are thirteen chiral centers, grouped as a stereotetrad (four contiguous chiral centers, C-2 to C-5)), an isolated chiral center (C-7), a stereotriad (three contiguous chiral centers (C-10 to C-12), and a stereopentad (five contiguous chiral centers, C-16 to C-20), and four olefinic bonds, three of which have specific geometry. The C-10 to C-12 stereotriad has syn, anti relative stereochemistry. This stereotriad (syn, anti) is also found within the stereotetrad and within the stereopentad.

The isolation of discodermolide from natural sources has not resulted in commercially meaningful quantities of the drug. Accordingly, there remains a continuing effort to find an efficient synthesis of discodermolide.

Because of the structural complexity of discodermolide, its synthesis has proven to be a formidable task. The synthesis of multigram quantities of discodermolide reported by Novartis in March 2004 required more than 20 steps in the longest linear sequence (more than 30 steps in total) and twenty months of work. See M. Freemantle, "Scaled-Up Synthesis of Discodermolide," *Chemical & Engineering News*, Mar. 1, 2004, pp. 33-35.

The Novartis synthesis as reported, like other published total syntheses, was based on the elaboration of the well-known chiral fungal product, methyl (R)-2-methyl-3-hydroxypropionate (the "Roche ester"), as the source of chirality for all three key intermediates.

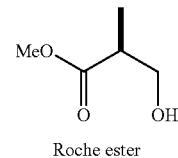

Roche ester

Recently, syntheses of key intermediates in which the source of chirality was a chiral auxiliary were reported. See Dias, Luiz C.; Bau, Rosana Z.; de Sousa, Marcio A.; Zukerman-Schpector, J. "High 1,5-Anti Stereoinduction in Boron-Mediated Aldol Reactions of Methyl Ketones" *Organic Letters* (2002), 4(24), 4325-4327 and Day, Billy W.; Kangani, Cyrous O.; Avor, Kwasi S. "Convenient syntheses of (2R,3S,4R)-3-(tert-butyldimethylsilanyloxy)-2,4-dimethyl-5-oxopentanoic acid methoxymethylamide from methacrolein. Preparation of C1-C7 and C17-C24 fragments of (+)-discodermolide." *Tetrahedron: Asymmetry* (2002), 13(11), 1161-1165. This approach was incorporated in the Novartis scale-up studies; see Loiseleur, Olivier; Koch, Guido; Wagner, Trixie. "A Practical Building Block for the Synthesis of Discodermolide." *Organic Process Research & Development* (2004), 8(4), 597-602 Also, recently, Myles and coworkers at Kosan prepared Smith's key intermediate, the common precursor "CP" by chemical modification of a fermentation product from a genetically engineered *Streptomyces*, see Burlingame, Mark A.; Mendoza, Esteban; Ashley, Gary W.; Myles, David C. "Synthesis of discodermolide intermediates from engineered polyketides" *Tetrahedron Letters* (2006), 47(7), 1209-1211.

There are other biologically active compounds which share some of the structural features of discodermolide. For example, the calyculins, natural products isolated from the marine sponge *Discodermia calyx* are inhibitors of serine-threonine phosphatase. Calyculins A and B are shown below. The encircled part of the structure shows a stereotetrad, that contains an anti, anti stereotriad at C-10 to C-12.

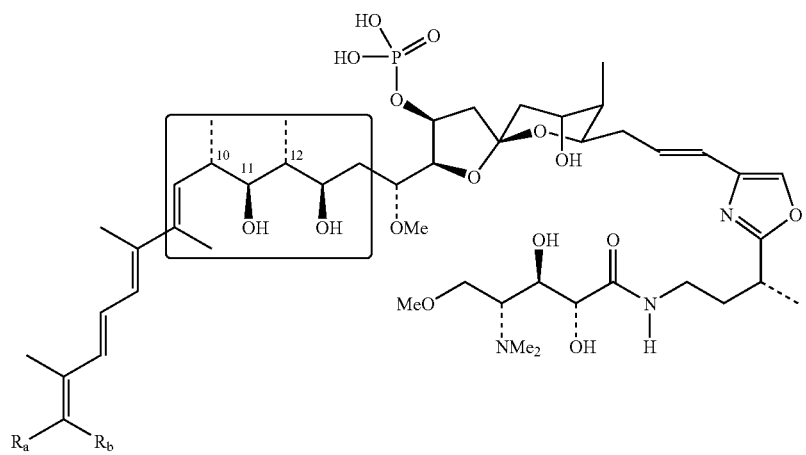

(+)-Calyculin A $R_a$ = H, $R_b$ = CN
(-)-Calyculin B $R_a$ = CN, $R_b$ = H

Likewise, the macrolide antitumor agent dictyostatin contains two syn, anti stereotriads, encircled in the picture, one of which is part of a stereotetrad.

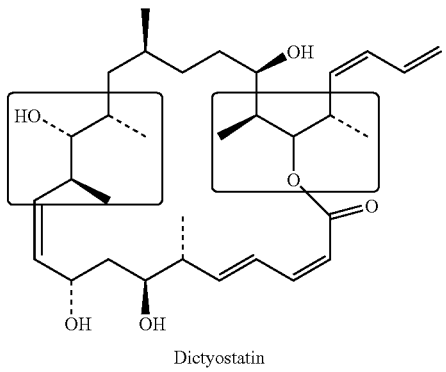

Dictyostatin

Accordingly, there is a clear need for more efficient ways to produce polypropionate antibiotics in which there are stereotriad regions. Such improved syntheses can be realized by, for example, providing new chemical intermediates. Particularly beneficial for this purpose are new intermediates which conveniently provide the anti, syn stereotriad that is contained, for example, in the C8 to C14 portion of discodermolide. Also particularly beneficial are schemes that rely on asymmetric catalysis, rather than on expensive chiral starting materials such as the Roche ester or on chiral auxiliaries for the introduction of chirality.

SUMMARY OF THE INVENTION

These, and other objectives as will be apparent to those of ordinary skill in the art, have been achieved by providing novel intermediate compounds of the formula:

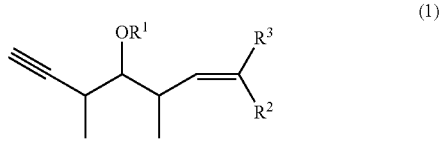
(1)

In formula (1), $R^1$ is H or a protecting group, and $R^2$ and $R^3$ each independently represents H, methyl, or a leaving group, provided that at least one of $R^2$ and $R^3$ is a leaving group.

In another embodiment, the invention relates to a compound having the formula:

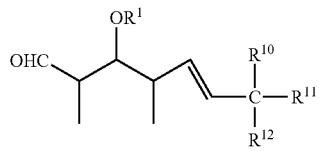

wherein:

$R^1$ represents H or a protecting group;

$R^{10}$ represents H or an alkyl group having 1-12 carbon atoms optionally substituted with one or more aryl groups, amino groups, halo groups, or $OR^{14}$ wherein $R^{14}$ represents an alkyl group having 1-12 carbon atoms; and $R^{11}$ and $R^{12}$ independently represent an alkyl group having 1-12 carbon atoms optionally substituted with one or more aryl groups, amino groups, halo groups, or $OR^{14}$ wherein $R^{14}$ represents an alkyl group having 1-12 carbon atoms; and wherein $R^{11}$ and $R^{12}$ may be connected to form a ring.

The intermediate compounds of formula (1) are useful for the synthesis of discodermolide, its derivatives, and related compounds.

DETAILED DESCRIPTION

The invention relates to compounds represented by the formula

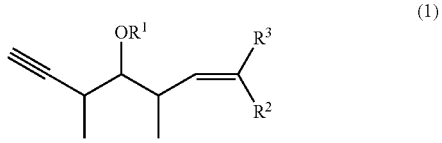
(1)

In one embodiment, $R^1$ in formula (1) represents hydrogen (H).

In another embodiment, $R^1$ represents a protecting group. The protecting group can be essentially any group suitable for the protection of an alcohol group as known in the art. In this specification, the phrase "protecting group" indicates any functionality that is used to replace a hydrogen on an alcohol and which can be removed with restoration of the hydrogen without altering the structure of the remainder of the molecule. Some examples are given below, but they are not meant to be inclusive.

An example of a class of suitable protecting groups for $R^1$ includes the class of silyl protecting groups. The class of silyl protecting groups, including silyl ether protecting groups, can be represented according to the formula:

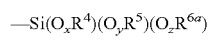

In the formula above for silyl ether protecting groups, $R^4$, $R^5$, and $R^6a$ each independently represents an alkyl group or an aryl group. The alkyl groups are preferably linear or branched, preferably having one to four carbon atoms, typically methyl, ethyl, isopropyl, butyl, and tertiary butyl. The aryl groups of $R^7$ are preferably phenyl, pyridinyl, pyrrolyl, or furanyl.

The subscripts x, y, and z independently represent 0 or 1. When x, y, or z is 0, the oxygen atom to which the subscript is associated is absent. When x, y, or z is 1, the oxygen atom to which the subscript is associated, is present.

Any two alkyl groups of $O_xR^4$, $O_yR^5$, and $O_zR^{6a}$, for example, $R^4$ and $R^5$, are optionally connected to form a silicon-containing ring. The carbon-carbon bond formed accompanies removal of a hydrogen atom from each carbon atom joined. The values of x and y are preferably both 0.

The size of the silicon-containing ring resulting from interconnection of two alkyl groups of $R^4$, $R^5$, and $R^{6a}$ depends on the size of the R groups that form the ring, and the value of x, y, and, as the case may be, z. Preferably, the ring includes two to six ring carbon atoms in addition to the silicon atom. For example, in one embodiment, $R^4$ and $R^5$ are both methyl groups and x and y are both 0. The methyl groups can be connected via their carbon atoms to form a silacyclopropane ring. In another embodiment, $R^4$ and $R^5$ are both ethyl groups and x and y are both 0. Depending on the connecting carbon atoms chosen, the ethyl groups can be connected to form a silacyclopentane ring or a 2-methylsilacyclobutane ring.

Some examples of silyl protecting groups according to the formula above for silyl ether protecting groups wherein x, y, and z are all 0 include triethylsilyl, tri-(n-propyl)silyl, tri-isopropylsilyl, tri-(n-butyl)silyl, triisobutylsilyl, t-butyldimethylsilyl (TBS), t-butyldiphenylsilyl, phenyldimethylsilyl, methyldiphenylsilyl, triphenylsilyl.

Some examples of silyl protecting groups according to the formula above wherein at least one of x, y, and z is 1 include trimethoxysilyl, dimethoxymethylsilyl, methoxydimethylsilyl, ethoxydimethylsilyl, methoxydiethylsilyl, isopropoxydimethylsilyl, phenoxydimethylsilyl, phenoxydiethylsilyl, methyldiphenoxysilyl, [2,4,6-tri-(t-butyl)phenoxy]dimethylsilyl, t-butoxydimethylsilyl, t-butoxydiphenylsilyl, (t-butyl)(methoxy)phenylsilyl, and methoxydiphenylsilyl.

Another example of a class of useful protecting groups for compounds of formula 1 is the acetal/ketal class. This class of protecting groups can be represented according to the formula:

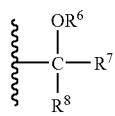

$R^6$ preferably represents an alkyl group optionally substituted with an aryl group; $R^7$ preferably represents hydrogen, an alkyl group, or an aryl group; and $R^8$ preferably represents hydrogen or an alkyl group. The alkyl groups of $R^6$, $R^7$, and $R^8$ are linear or branched, preferably having one to four carbon atoms, typically methyl or ethyl. The alkyl groups of $R^6$ and $R^7$ may be joined to form a five or six member saturated ring. The aryl substituent of $R^6$ and the aryl group of $R^7$ are preferably phenyl, pyridinyl, pyrrolyl, or furanyl.

Some preferred acetal/ketal protecting groups include methoxymethyl, ethoxymethyl, tetrahydropyranyl, and benzyloxymethyl. Some additional protecting groups in this class include p-methoxybenzyloxymethyl and beta-trimethylsilyloxyethoxymethyl (SEM) groups.

Another example of a class of suitable protecting groups includes arylmethyl protecting groups, which protect a hydroxyl group by converting it to an arylmethyl ether. The aryl group may be phenyl, pyridinyl, pyrrolyl, or furanyl, optionally substituted with methoxy, ethoxy, nitro, or halo (F, Cl, Br, or I). Some preferred members of this class of protecting groups include benzyl, p-methoxybenzyl, and p-ethoxybenzyl.

Other suitable protecting groups are reviewed in *Protecting groups* by Kocienski, Philip J. Stuttgart; New York: Georg Thieme, c2005 and in *Protective groups in organic synthesis* by Greene, Theodora W. and Wuts, Peter G. M. New York: Wiley, c1999.

In formula (1), $R^1$ and $R^3$ each independently represent H, methyl, or a leaving group. At least one of $R^2$ and $R^3$ is a leaving group. Preferably, only one of $R^2$ and $R^3$ is a leaving group.

For example, $R^2$ can be a methyl group or H, and $R^3$ a leaving group; and $R^3$ can be a methyl group or H, and $R^2$ a leaving group.

The leaving group is essentially any group capable of being replaced by a carbon substituent under conditions to which the protecting group is stable. For example, the leaving group can be a halogen atom. Some suitable halogen atoms include chloride, bromide, and iodide.

Alternatively, the leaving group can be organic in nature, such as, for example, a sulfonate ester group or a phosphorus ester group. Some examples of sulfonate ester groups include triflate, mesylate, tosylate, and benzenesulfonate. Examples of phosphorus ester groups include phosphates.

In one embodiment, the compounds belong to the class of Z-isomer intermediate compounds. In one example of a Z-intermediate compound, $R^1$ is a protecting group, $R^3$ is a methyl group and $R^2$ is a leaving group. These compounds are useful for the synthesis of (+)-discodermolide and its derivatives.

In another embodiment of a Z-intermediate compound, $R^1$ in formula (1) is a protecting group, while $R^3$ is H and $R^2$ is a leaving group. These compounds are intermediates for the synthesis of, inter alia, the 14-normethyl analog of discodermolide and its derivatives. More specifically, these compounds are intermediates for the synthesis of 13,14-cis-14-normethyl discodermolide and its analogs.

The intermediate compounds of formula (1) contain carbons 8 to 14 (i.e., C8-C14) of discodermolide. The carbon atom that corresponds to C14 of discodermolide is attached to $R^2$ and $R^3$ in formula (1). In order to produce discodermolide, the compounds according to formula (1) must be treated with other compounds which provide the C1-C7 and C15-C24 portions of discodermolide. A suitable protocol for doing so is shown in schemes 1-3 below.

The term "discodermolide" as used herein refers to (+)- or (−)-discodermolide as well as any stereoisomeric and structural derivatives within the scope of the invention. Also included are mixtures of (+)- and (−)-discodermolide in any ratio. For example, the mixture can be a racemic mixture of (+)- and (−)-discodermolide.

The E-isomer intermediate compounds are also useful, for example in the synthesis of the calyculins. Specifically, the E-isomer intermediates can provide the stereotriad portion of the calyculin compounds. Some examples of particularly relevant E-isomer intermediate compounds according to formula (1) include those shown below in formulas 1a and 1b below.

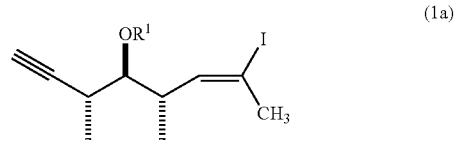

(1a)

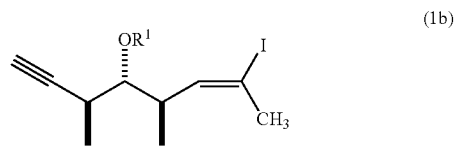

(1b)

The compound according to formula (1) contains three adjacent stereocenters, i.e., a stereotriad. For the synthesis of (+)-discodermolide and its derivatives, the compound according to formula (1) is more specifically represented as:

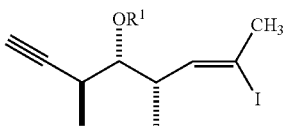

(1c)

wherein R¹ has the same meaning as above.

An example of a particularly preferred compound according to formula (1c) includes the structures according to formula (1d) and (1e):

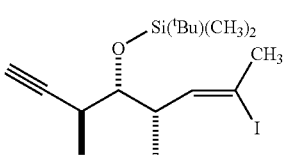

(1d)

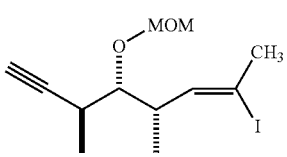

(1e)

wherein MOM represents methoxymethyl.

In addition to the stereoisomeric configuration shown in formula (1c), the invention also includes any of the other possible stereoisomeric configurations. Other stereoisomeric configurations are useful for producing the corresponding (−)- or epi-discodermolide derivatives. For example, the stereochemically inverted analog of formula (1c), as shown below in formula (1f), can be used to make (−)-discodermolide.

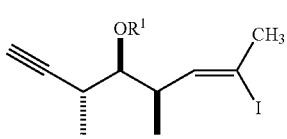

(1f)

The deprotected alcohol compounds, i.e., when R¹ in formula (1) is H, can be used, inter alia, as a storable precursor to the corresponding protected derivatives. The corresponding alcohols can be represented by formula (1g) below where $R^2$ and $R^3$ are as previously defined.

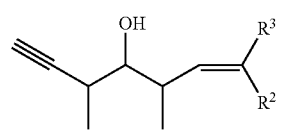

(1g)

The deprotected alcohol compounds can be synthesized by, for example, deprotection of the corresponding protected compounds by any suitable means known in the art. For example, deprotection can be achieved by hydrolysis of an acetal or silyl ether with an acid.

In one embodiment, formula (1) represents any of the stereoisomeric compounds, as described above. In another embodiment, formula (1) represents a mixture, such as a racemic mixture, of two or more compounds having the structure of formula (1). For example, formula (1) can represent a combination of compounds according to formulas (1c) and (1f).

In addition, when formula (1) represents more than one stereoisomeric compound, the compounds can be in any suitable proportion to each other. For example, a combination of stereoisomeric compounds, such as that of formulas (1c) and (1f) can be in proportions of approximately 50:50, 40:60, 30:70, 20:80, 10:90, 5:95, 1:99, and so on.

The synthesis of intermediate compounds according to formula (1) can be accomplished by any suitable synthetic method known in the art. In a preferred embodiment, the intermediate compounds can be synthesized according to Scheme 1.

Scheme 1. Synthesis of compounds 1d and 1e which have formula (1)

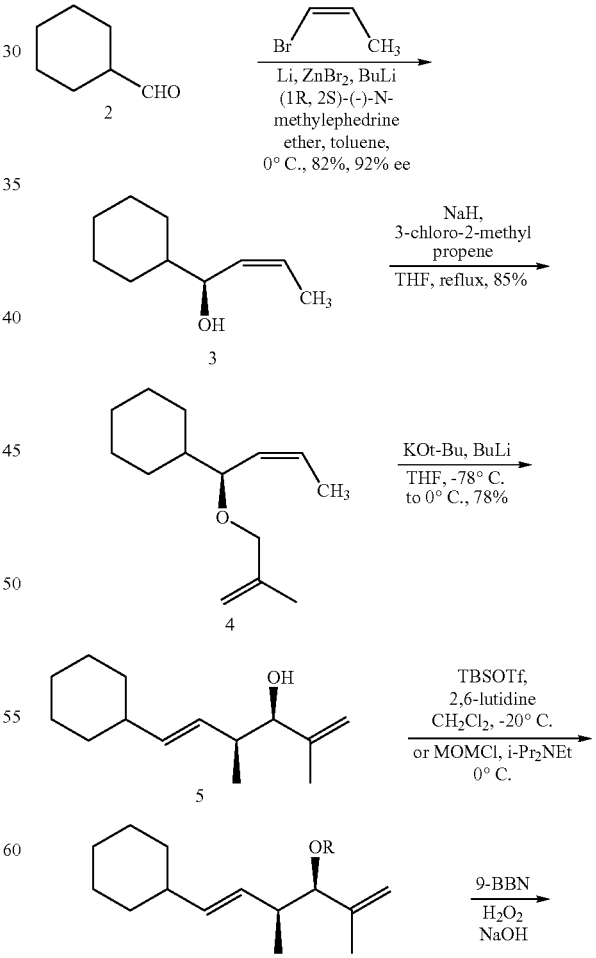

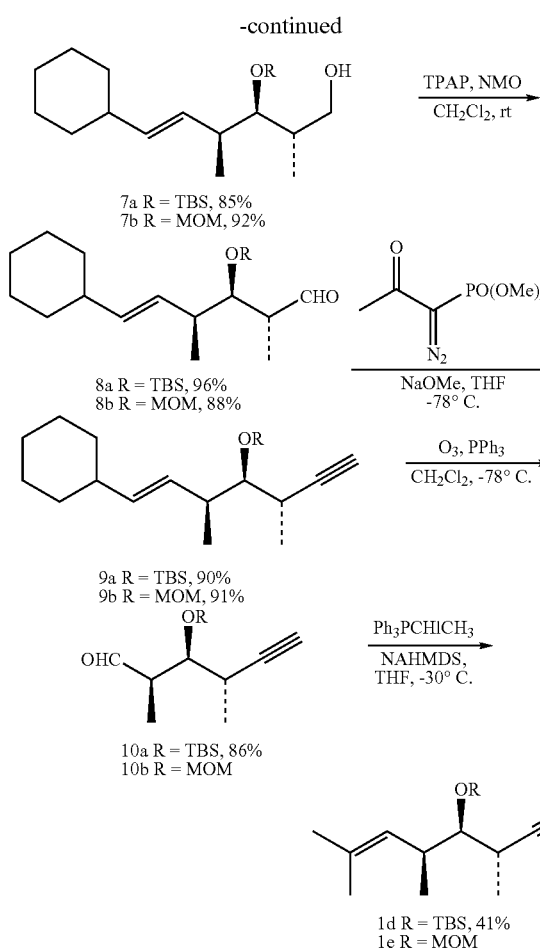
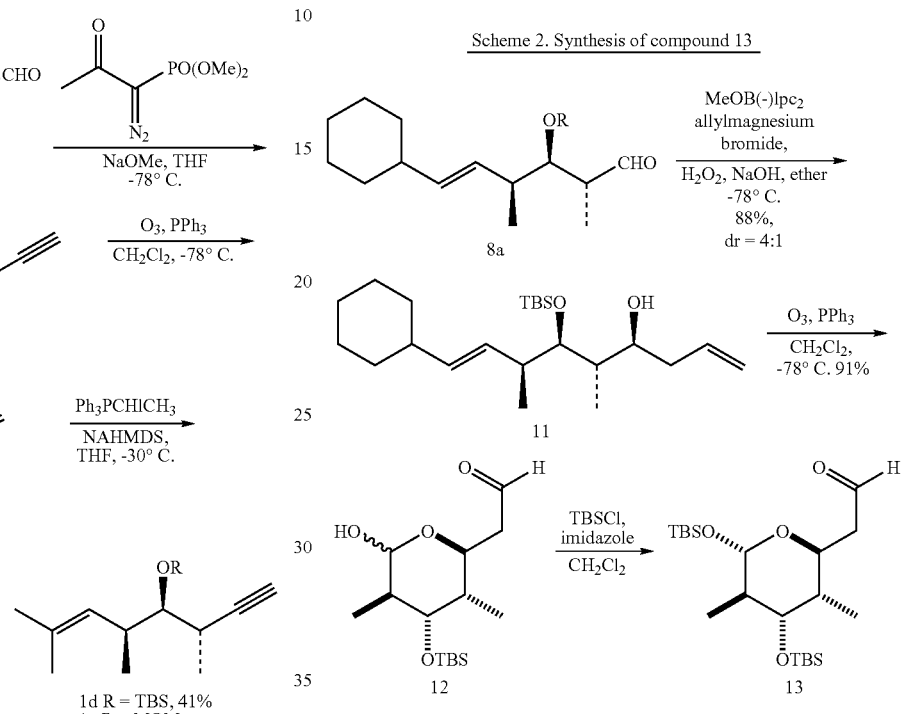
The compounds according to formula (1) allow for the convenient synthesis of discodermolide and its derivatives by methods known in the art. For example, when the building block 1d is used in conjunction with building block 13, available as shown in Scheme 2, discodermolide is conveniently synthesized by the sequence shown in Scheme 3.
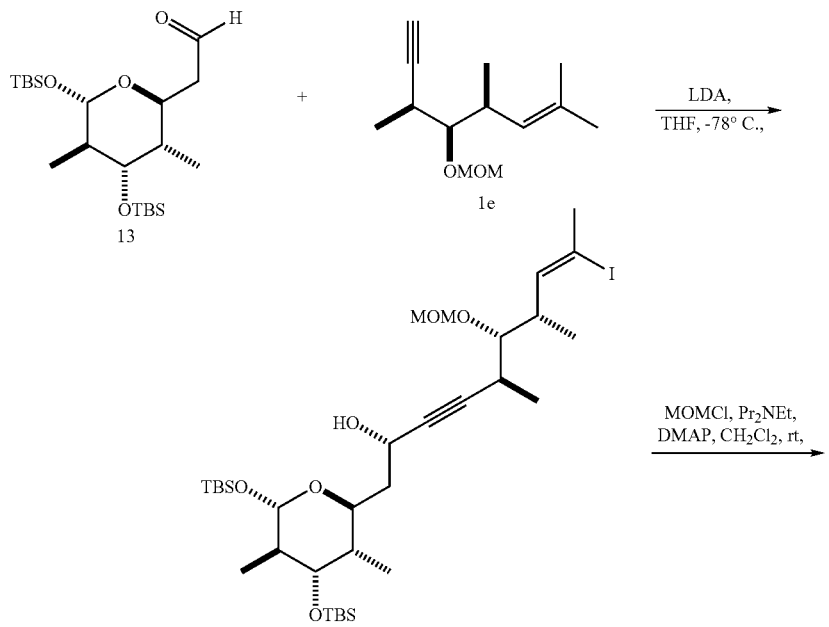

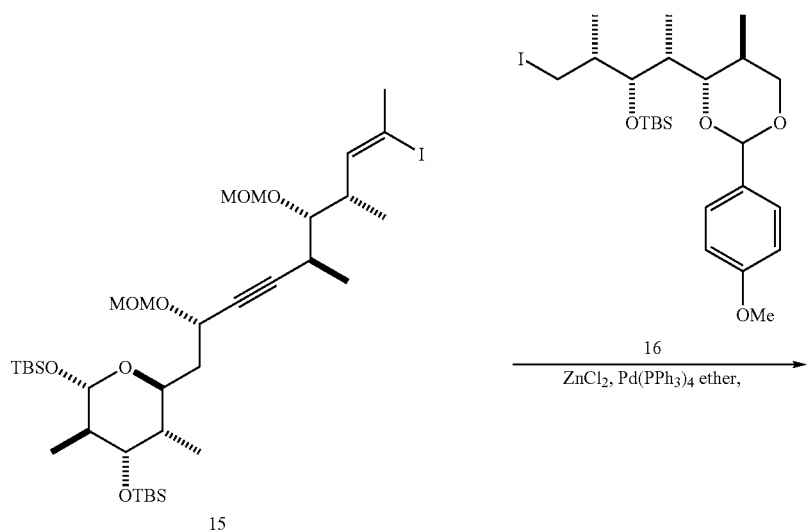
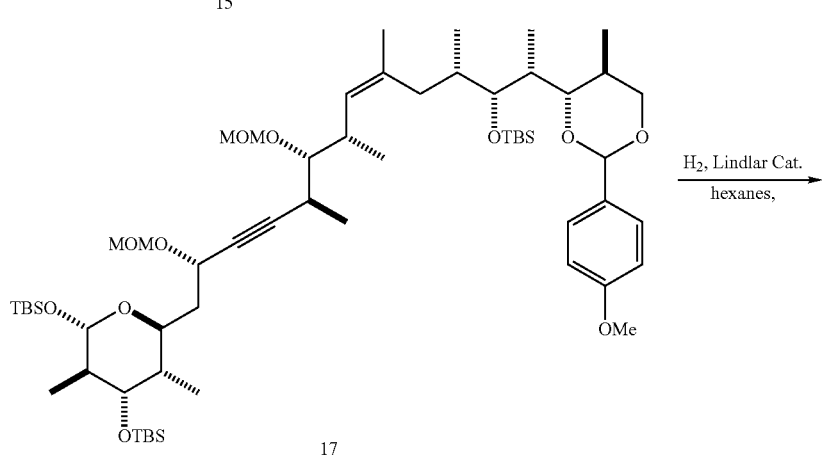
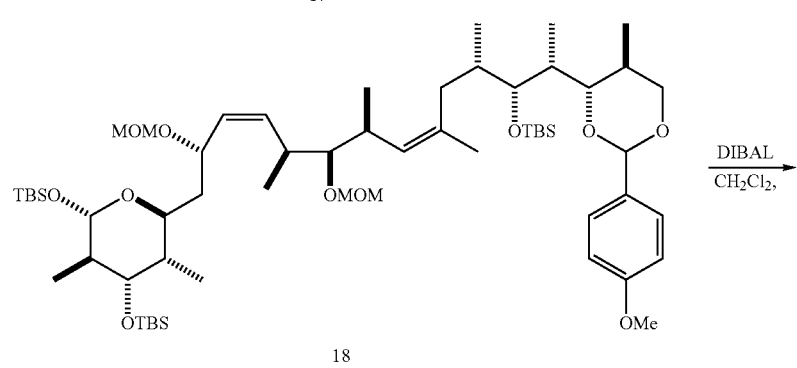
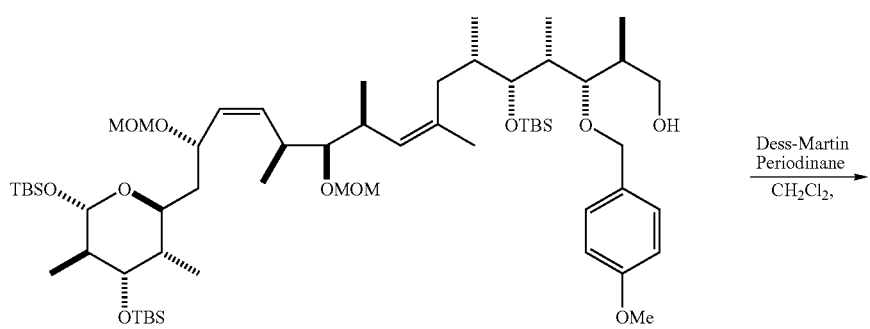

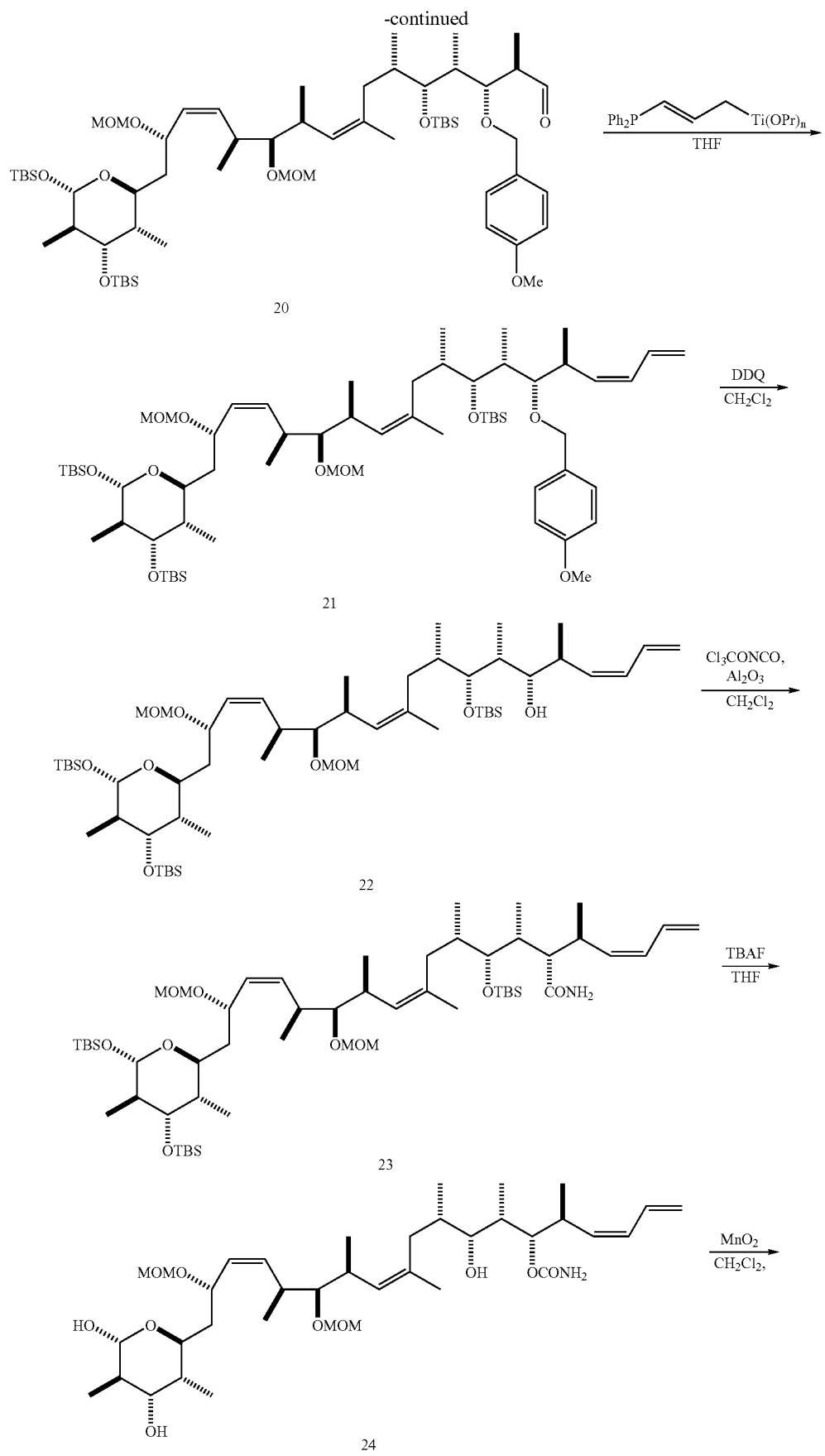

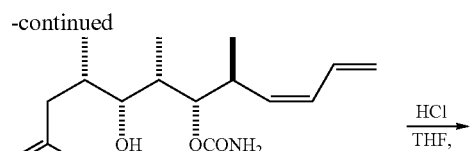
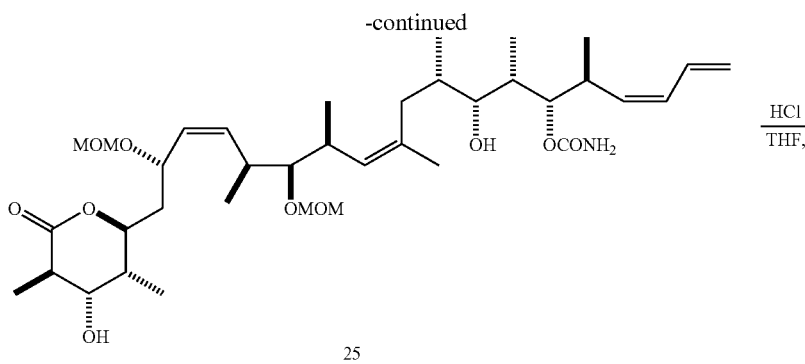

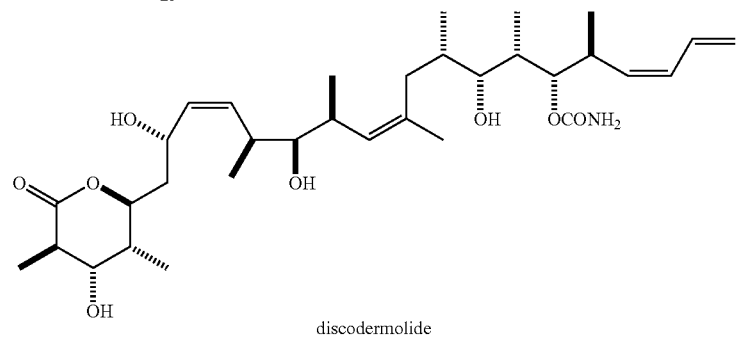

discodermolide

As can be seen in scheme 1, compounds having general formula 1 are conveniently prepared from compounds having general formula 8, wherein $R^1$ has the meaning described above.

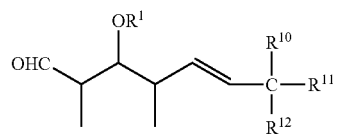

For example, compounds having general formula 8 wherein R1 represents H (8g) correspond to formula 1g.

A particular stereochemical isomer of structure 1 can be prepared from the corresponding stereochemical isomer of formula 8. For example, compounds having formulas 1d and 1e are conveniently prepared from compounds having formulas 8a and 8b, respectively. See scheme 1.

More generally, formula 8c below corresponds to formula 1c above.

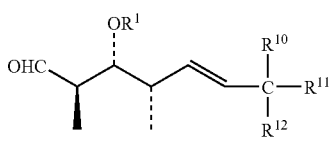

Therefore, compounds having formulas 1d and 1e, above, are conveniently synthesized from compounds having formula 8c when $R^1$ in 8c represents $Si(^tBu)(CH_3)_2$ (formula 8d) or MOM (8e), respectively. These intermediates are useful in preparing (+)-discodermolide.

Correspondingly, compounds having formula 8f may be used to prepare compounds having formula 1f.

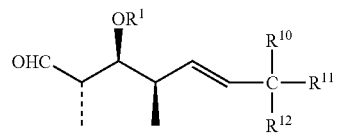

Compounds having formula 1f are useful in preparing (−)-discodermolide.

Preferred methods for fulfilling the reaction steps given above are provided in the examples below. The examples below are for the purpose of illustration. Accordingly, the scope of the invention is not to be in any way limited by the examples given below.

The Racemic Series (Scheme 1)

EXAMPLE 1

Racemic Cis Allylic Alcohol (3)

A solution of cyclohexanecarboxaldehyde (2) (2.33 g, 20.8 mmol) in 40 mL of THF was cooled to −40° C. 1-Propynylmagnesium bromide (0.5 M in THF, 50.0 mL was added dropwise. After adding, the temperature of the reaction mixture was increased to 0° C. and stirred for 2 h. The reaction was quenched with saturated aqueous ammonium chloride solution. The water phase was extracted with ether (3×20 mL). The combined organic layers were washed with brine, dried over $MgSO_4$, filtered, and concentrated. The crude product was chromatographed (HE: EA=10:1) to provide 2.78 g (88%) of the propargyl alcohol as an oil. $^1H$ NMR (300 MHz, $CDCl_3$) 4.10 (m, 1H), 1.85 (d, J=2.1 Hz, 3H), 1.80-1.65 (m, 5H), 1.58-1.20 (m, 1H), 1.30-0.98 (m, 6H); $^{13}$C NMR (300 MHz, CDCl$_3$) 81.6, 79.5, 67.5, 44.4, 28.7, 28.2, 26.5, 26.02, 26.00, 3.7.

A solution of the propargyl alcohol from the above experiment (380 mg, 2.5 mmol) in hexane (3 mL) was treated with Pd/CaCO$_3$ poisoned with Pb, (5% Pd, 30 mg) and quinoline (64 µL). Hydrogen was bubbled through the reaction mixture for 20 min, and the resultant suspension was stirred vigorously for 24 h under 1 atm of H$_2$. After filtration through Celite with Et$_2$O, the solvents were removed in vacuo. Chromatography (HE: EA=10:1) gave racemic alcohol (3) (346 mg, 90%) as a clear liquid. $^1$H NMR (300 MHz, CDCl$_3$) 5.57 (dqd, J=10.2, 6.8, 1.3 Hz, 1H), 5.36 (ddq, J=10.2, 9.4, 1.8 Hz, 1H), 4.14 (dd, J=8.4 Hz, 1.0 Hz, 1H), 1.90 (m, 1H), 1.80-1.58 (m, 8H), 1.58-0.80 (m, 6H); $^{13}$C NMR (300 MHz, CDCl$_3$) 132.4, 126.9, 71.7, 44.3, 29.0, 28.6, 26.8, 26.3, 26.2, 13.7. IR 3365 (broad), 2923, 28523, 1449, 1022, 994.

EXAMPLE 2

Racemic Ether (4)

A 100-mL reaction flask was charged with 95% sodium hydride (2.76 g, 109 mmol) and 20 mL of dry THF. Racemic alcohol 3 (2.40 g, 15.6 mmol) in 2 mL of THF was added dropwise followed by 3-chloro-2-methylpropene (4.24 g, 46.8 mmol). The reaction mixture was stirred at reflux overnight and then cooled to room temperature. Excess sodium hydride was quenched by the slow addition of 3 mL of water. The resulting mixture was poured into water. Ether extracts (30 mL×3) were combined and the resulting organic solution was dried over MgSO$_4$, filtered, and concentrated. Chromatography (HE: EA=30:1) produced a colorless oil (2.78 g, 85%). $^1$H NMR (300 MHz, CDCl$_3$) 5.73 (dqd, J=10.2, 6.8, 1.3 Hz, 1H), 5.24 (ddq, 10.2, 9.4, 1.8 Hz, 1H), 4.93 (m, 1H), 4.85 (m, 1H), 3.90 (d, J=12.6 Hz, 1H), 3.80 (m, 1H), 3.69 (d, J=12.4 Hz, 1H), 1.96 (m, 1H), 1.73 (s, 3H), 1.70-1.65 (m, 5H), 1.62 (dd, J=7.1, 2.0 Hz, 3H), 1.58-0.80 (m, 6H); $^{13}$C NMR (300 MHz, CDCl$_3$) 143.3, 130.9, 128.1, 112.1, 77.9, 72.0, 43.1, 31.9, 29.7, 28.9, 27.0, 26.5, 26.4, 23.0, 20.0, 14.4, 13.9. IR 2971, 2922, 2852, 1449, 1085, 896.

EXAMPLE 3

Racemic Dienol (5)

Potassium tert-butoxide (1.0 M in THF, 5.5 mL, 5.5 mmol) was added to a flask under argon and an additional 5.0 mL of THF was added. The solution was cooled to −78° C. and ether (4) (5.0 mmol, 1.05 g) was added. n-Butyllithium (1.6M in THF, 3.8 mL, 6.1 mmol) was slowly added. The mixture was warmed to −20° C. over 4 h and the stirred 12 h at −20° C. and 2 h at 0° C. The reaction was quenched with water and the resulting mixture was extracted with ether. The organic phase was dried over MgSO$_4$ and concentrated. Chromatography (HE: EA=10:1) gave a colorless oil (819 mg, 78%). $^1$H NMR (300 MHz, CDCl$_3$) 5.40 (dd, J=16.2, 6.6 Hz, 1H), 5.31 (dd, J=16.2, 6.6 Hz, 1H), 4.92 (m, 1H), 4.86 (m, 1H), 3.87 (d, J=20.0 Hz, 1H), 2.33 (m, 1H), 1.90 (m, 1H), 1.69 (s, 3H), 1.68-1.65 (m, 5H), 1.32-1.05 (m, 6H), 0.97 (d, J=6.9 Hz, 3H); $^{13}$C NMR (300 MHz, CDCl$_3$) 146.2, 137.4, 129.7, 112.1, 79.3, 41.0, 40.1, 33.5, 33.4, 26.5, 26.4, 18.9, 14.8. IR 3403 (broad), 2965, 2924, 2851, 1448, 979, 968, 896.

EXAMPLE 4

Racemic Silyl Ether (6)

A mixture of racemic alcohol 5 (550 mg, 2.62 mmol), imidazole (446 mg, 6.55 mmol), t-BuMe$_2$SiCl (592 mg, 3.93 mmol) and DMAP (80.5 mg, 0.66 mmol) in 3 mL of DMF was stirred overnight. The mixture was partitioned between ether (50 mL) and water (3×15 mL). The combined water solution was extracted with ether (2×25 mL) and then the combined organic solution was dried over MgSO$_4$, filtered, and concentrated. Chromatography (HE: EA=30:1) gave a colorless oil (704 mg, 83%). $^1$H NMR (300 MHz, CDCl$_3$) 5.30 (dd, J=16.1, 6.6 Hz, 1H), 5.19 (dd, J=16.1, 6.6 Hz, 1H), 4.78 (m, 1H), 4.75 (m, 1H), 3.71 (d, J=7.0 Hz, 1H), 2.17 (m, 1H), 1.88 (m, 1H), 1.75-1.64 (m, 4H), 1.63 (s, 3H), 1.32-0.96 (m, 6H), 0.94 (d, J=7.0 Hz, 3H), 0.89 (s, 9H), 0.02 (s, 3H), −0.03 (s, 3H); $^{13}$C NMR (300 MHz, CDCl$_3$) 146.9, 135.7, 130.8, 112.1, 81.5, 41.3, 41.0, 33.43, 33.37, 26.6, 26.4, 26.2, 18.6, 18.1, 16.4, −4.3, −4.7. IR 2957, 2927, 2854, 1449, 1251, 1071, 896, 867.

EXAMPLE 5

Racemic Alcohol (7a)

To the silyl ether (380 mg, 1.17 mmol) in 1 mL of THF was added 9-BBN (0.5 M in THF, 2.80 mL, 1.40 mmol) at −20° C. After 10 min the reaction mixture was warmed to room temperature and stirring was continued for 6 h. TLC showed the completion of the reaction. Then 0.6 mL of 3 N NaOH was added and this was followed by 0.6 mL of 30% H$_2$O$_2$. The resulting mixture was stirred for 12 hours at room temperature and then poured into 20 mL of ether and 5 mL of saturated aqueous sodium chloride. The aqueous phase was extracted with ether and the organic solutions were combined, dried over MgSO$_4$, and concentrated. Chromatography (HE: EA=10:1) gave a colorless oil (340 mg, 85%). $^1$H NMR (300 MHz, CDCl$_3$) 5.36, (m, 2H), 3.72 (dd, J=11.0, 3.8 Hz, 1H), 3.52 (dd, J=11.0, 5.7 Hz, 1H), 3.49 (dd, J=3.9, 6.1 Hz), 2.42-2.30 (m, 2H), 1.76-1.58 (m, 4H), 1.32-1.02 (m, 6H), 1.00 (d, J=7.1 Hz, 3H), 0.92 (s, 9H), 0.11 (s, 3H), 0.09 (s, 3H). $^{13}$C NMR (300 MHz, CDCl$_3$) 136.9, 130.3, 81.9, 65.9, 42.3, 41.1, 37.5, 33.37, 33.35, 26.5, 26.4, 18.5, 17.2, 16.7, −3.6, −3.7. IR 3398 (broad), 2957, 2927, 1254, 1074, 1024.

EXAMPLE 6

Racemic Aldehyde (8a)

To a stirred mixture of racemic alcohol (7a) (177 mg, 0.52 mmol) and powdered molecular sieves 4A (518 mg) in 10 mL of methylene chloride was added 182 mg (1.55 mmol) 4-methylmorpholine N-oxide (NMO) followed by 12.7 mg, 36.2 µmmol tetrapropylammonium perruthenate (TPAP). After stirring at room temperature for 20 minutes, the mixture was filtered through a silica gel column (HE: EA=10:1) gave aldehyde 8a (170 mg, 96%) as a colorless oil. $^1$H NMR (300 MHz, CDCl$_3$) 9.69 (d, J=1.9 Hz, 1H), 5.39 (dd, J=15.4, 6.0 Hz, 1H), 5.16 (ddd, J=15.4, 8.0, 1.1 Hz), 3.75 (dd, J=6.9, 3.3 Hz, 1H), 2.51 (m, 1H), 2.37 (m, 1H), 1.87 (m, 1H), 1.73-1.60 (m, 4H), 1.32-1.02 (m, 6H), 1.11 (d, J=6.9 Hz, 3H), 0.99 (d, J=6.9 Hz, 3H), 0.88 (s, 9H), 0.08 (s, 3H), 0.06 (s, 3H); $^{13}$C NMR (300 MHz, CDCl$_3$) 204.8, 138.5, 129.3, 78.8, 50.7, 41.9, 41.0, 33.0, 32.9, 26.5, 26.3, 26.2, 18.5, 17.6, 11.4, −3.8, −4.1. IR 2956, 2928, 2854, 1724, 1255, 1079, 1038, 852.

EXAMPLE 7

Racemic Acetylene (9a)

To a cooled (−78° C.) solution of potassium tert-butoxide (1.0 M in THF, 600 µL, 0.60 mmol) was added dimethyl diazomethylphosphonate (150 mg, 1.0 mmol) in 1 mL of THF via cannula. After stirring for 10 min, a solution of racemic aldehyde (8) (170 mg, 0.50 mmol) in 2 mL of THF was added via cannula. The reaction was stirred at −50° C. for 20 h and then 1 h at ambient temperature for 1 h. The reaction volume was reduced to approximately 1 mL and directly chromatographed (HE: EA=50:1) to afford acetylene 9 (117.6 mg, 70%) as colorless oil. $^1$H NMR (300 MHz, CDCl$_3$) 5.39 (dd, J=15.4, 5.8 Hz, 1H), 5.27 (dd, J=15.6, 7.6 Hz, 1H), 3.37 (dd, J=6.7, 3.6 Hz, 1H), 2.65 (m, 1H), 2.39 (m, 1H), 2.02 (dd, J=2.4, 0.80 Hz), 1.92 (m, 1H), 1.74-1.60(m, 4H), 1.32-1.02 (m, 6H), 1.17 (d, J=7.1 Hz, 3H), 0.97 (d, J=6.9 Hz, 3H), 0.91 (s, 9H), 0.07 (s, 3H), 0.06 (s, 3H). $^{13}$C NMR (300 MHz, CDCl$_3$) 136.3, 131.2, 87.2, 79.1, 70.3, 41.7, 41.0, 33.3, 33.2, 31.7, 26.6, 26.41, 26.39, 18.7, 17.9, 17.4, −3.4, −3.6. IR 3312, 2957, 2927, 2854, 1253, 1080, 860.

EXAMPLE 8

Racemic Aldehyde (10a)

A solution of Sudan red 7B (1 mg/mL, 20 µL) was added to a solution of racemic acetylene (9a) (52.5 mg, 0.15 mmol in 4 mL of methylene chloride). The solution was cooled to −78° C. and flushed with argon for 5 min. A flow of ozone was passed through the solution until the pink color disappeared (ca, 5 min). The remaining ozone was then purged with argon for 10 min, and then 1 mL of dimethyl sulfide was added. After stirring for 1 h at −78° C. and then 2 h at ambient temperature, the solution was concentrated in vacuo. Chromatography (HE: EA=40:1) gave a colorless oil (28.8 mg, 75%). $^1$H NMR (300 MHz, CDCl$_3$) 9.89 (d, J=0.90 Hz, 1H), 4.08 (m, 1H), 2.76-2.60 (m, 2H), 2.10 (d, J=2.7 Hz, 1H), 1.22 (d, J=7.1 Hz, 3H), 1.12 (d, J=7.1 Hz, 3H), 0.90 (s, 9H), 0.11 (s, 3H), 0.06 (s, 3H). IR 3312, 2957, 2927, 2854, 1253, 1080, 860.

The Chiral Series (Scheme 1)

EXAMPLE 9

(S)-Allylic Alcohol (3)

To lithium powder (562 mg, 81 mmol) under argon was added dry ether (50 mL). The suspension was cooled to −35° C. With stirring, a solution of (Z)-1-bromo-propene (4.84 g, 40 mmol) was added dropwise. The resulting mixture was stirred at −35° C. for 2 h and then treated dropwise with zinc bromide solution (0.6 M in ether, 77 mL, 44 mmol). The reaction mixture was stirred for an additional 1 h at 0° C. and then a solution of lithium (1R, 2S)-N-methylephedrate, prepared by the addition of n-butyllithium (2.5M in hexanes, 16.4 mL, 41 mmol) to a solution of (−)—N-methylephedrine (7.35 g, 41 mmol) in toluene (100 mL) at 0° C., was added by cannula. The solution was stirred for 1 h at 0° C. and then cyclohexanecarboxaldehyde (3.20 g, 28.6 mmol) was added neat. After stirring for 1 h at 0° C., the reaction was quenched by the addition of saturated aqueous ammonium chloride solution. The organic phase was separated and the aqueous phase was extracted with ether. The combined organic solution was washed with a second portion of ammonium chloride solution, dried over MgSO$_4$, and concentrated. Chromatography (HE: EA=10:1) gave alcohol (S)-3 (3.61 g, 82%, 92% ee. according to NMR study of Mosher ester) as a clear liquid. $^1$H NMR (300 MHz, CDCl$_3$) 5.57 (dqd, J=10.2, 6.8, 1.3 Hz, 1H), 5.36 (ddq, J=10.2, 9.4, 1.8 Hz, 1H), 4.14 (dd, J=8.4 Hz, 1.0 Hz, 1H), 1.90 (m, 1H), 1.80-1.58 (m, 8H), 1.58-0.80 (m, 6H); $^{13}$C NMR (300 MHz, CDCl$_3$) 132.4, 126.9, 71.7, 44.3, 29.0, 28.6, 26.8, 26.3, 26.2, 13.7. IR 3365 (broad), 2923, 28523, 1449, 1022, 994.

EXAMPLE 10

(S)-Ether (4)

A 100-mL reaction flask was charged with 95% sodium hydride (3.49 g, 146 mmol) and 30 mL of dry THF. Chiral alcohol 3 (3.20 g, 20.8 mmol) in 3 mL of THF was added dropwise followed by 3-chloro-2-methylpropene (5.65 g, 62.4 mmol). The reaction mixture was stirred at reflux overnight and then cooled to room temperature. Excess sodium hydride was quenched by the slow addition of 5 mL of water. The resulting mixture was poured into water. Ether extracts (50 mL×3) were combined and the resulting organic solution was dried over MgSO$_4$, filtered, and concentrated. Chromatography (HE: EA=30:1) produced a colorless oil (3.68 g, 85%). $^1$H NMR (300 MHz, CDCl$_3$) 5.73 (dqd, J=10.2, 6.8, 1.3 Hz, 1H), 5.24 (ddq, 10.2, 9.4, 1.8 Hz, 1H), 4.93 (m, 1H), 4.85 (m, 1H), 3.90 (d, J=12.6 Hz, 1H), 3.80 (m, 1H), 3.69 (d, J=12.4 Hz, 1H), 1.96 (m, 1H), 1.73 (s, 3H), 1.70-1.65 (m, 5H), 1.62 (dd, J=7.1, 2.0 Hz, 3H), 1.58-0.80 (m, 6H); $^{13}$C NMR (300 MHz, CDCl$_3$) 143.3, 130.9, 128.1, 112.1, 77.9, 72.0, 43.1, 31.9, 29.7, 28.9, 27.0, 26.5, 26.4, 23.0, 20.0, 14.4, 13.9. IR 2971, 2922, 2852, 1449, 1085, 896.

EXAMPLE 11

Chiral Dienol (5)

Potassium tert-butoxide (1.0 M in THF, 17.5 mL, 17.5 mmol) was added to a flask under argon and an additional 15.0 mL of THF was added. The solution was cooled to −78° C. and chiral ether 4 (16.0 mmol, 3.35 g) was added. n-Butyllithium (1.6M in THF, 12.1 mL, 19.3 mmol) was slowly added. The mixture was warmed to −20° C. over 4 h and the stirred 12 h at −20° C. and 2 h at 0° C. The reaction was quenched with water and the resulting mixture was extracted with ether. The organic phase was dried over MgSO$_4$ and concentrated. Chromatography (HE: EA=10:1) gave a colorless oil (2.68 g, 80%). $^1$H NMR (300 MHz, CDCl$_3$) 5.40 (dd, J=16.2, 6.6 Hz, 1H), 5.31 (dd, J=16.2, 6.6 Hz, 1H), 4.92 (m, 1H), 4.86 (m, 1H), 3.87 (d, J=20.0 Hz, 1H), 2.33 (m, 1H), 1.90 (m, 1H), 1.69 (s, 3H), 1.68-1.65 (m, 5H), 1.32-1.05 (m, 6H), 0.97 (d, J=6.9 Hz, 3H); $^{13}$C NMR (300 MHz, CDCl$_3$) 146.2, 137.4, 129.9, 112.1, 79.3, 41.0, 40.1, 33.5, 33.4, 26.5, 26.4, 18.9, 14.8. IR 3403 (broad), 2965, 2924, 2851, 1448, 979, 968, 896.

EXAMPLE 12

Chiral Silyl Ether (6a)

A mixture of chiral dienol 5 (1.27 g, 6.13 mmol) and 2,6-lutidine (1.15 g, 1.25 mL, 10.7 mmol) in 20 mL of methylene chloride was cooled to −20° C. t-BuMe$_2$SiOTf where Tf=triflate (1.86 g, 1.62 L, 7.05 mmol) was added over 5 min. The mixture was stirred for 1 hour at −20° C. and 30 min at room temperature. The mixture was diluted with 40 mL of ether and poured into 25 mL of 1 M NaHSO$_4$ solution. The resulting layers were separated and water phase was extracted with ether. The combined organic solution was washed with 1 M NaHSO$_4$ solution, sodium bicarbonate and brine. The solution was then dried over MgSO$_4$, filtered, and concentrated. Chromatography (HE: EA=30:1) gave a colorless oil (1.83 g, 92%). $^1$H NMR (300 MHz, CDCl$_3$) 5.30 (dd, J=16.1, 6.6 Hz, 1H), 5.19 (dd, J=16.1, 6.6 Hz, 1H), 4.78 (m, 1H), 4.75 (m, 1H), 3.71 (d, J=7.0 Hz, 1H), 2.17 (m, 1H), 1.88 (m, 1H), 1.75-1.64 (m, 4H), 1.63 (s, 3H), 1.32-0.96 (m, 6H), 0.94 (d, J=7.0 Hz, 3H), 0.89 (s, 9H), 0.02 (s, 3H), −0.03 (s, 3H); $^{13}$C NMR (300 MHz, CDCl$_3$) 146.9, 135.7, 130.8, 112.1, 81.5, 41.3, 41.0, 33.43, 33.37, 26.6, 26.4, 26.2, 18.6, 18.1, 16.4, −4.3, −4.7. IR 2957, 2927, 2854, 1449, 1251, 1071, 896, 867.

EXAMPLE 13

Chiral MOM Ether (6b)

MOMCl (567 mg, 535 μL, 7.05 mmol) was added via syringe dropwise to a solution of chiral alcohol 5 (296 mg, 1.41 mmol) in 8 mL of methylene chloride at 0° C., followed by addition of $^i$Pr$_2$NEt (911 mg, 1.23 mL, 7.05 mmol). The resulting mixture was stirred at 0° C. for 2 h and then at ambient temperature for 16 h. Saturated solution of sodium carbonate (4 mL) was added to quench the reaction. The aqueous phase was extracted with methylene chloride (25 mL×3) and the organic phases were combined, dried (MgSO$_4$), and concentrated. Chromatography (HE: EA=10: 1) gave chiral MOM ether 6b as a colorless oil (323 mg, 90%). $^1$H NMR (300 MHz, CDCl$_3$) δ 5.35 (dd, J=15.6, 6.6 Hz, 1H), 5.17 (dd, J=12.6, 7.8 Hz, 1H), 4.91 (d, J=0.9 Hz, 1H), 4.84 (s, 1H), 4.61 (m, 1H), 4.47 (d, J=6.6 Hz, 1H), 3.67 (d, J=7.2 Hz, 1H), 3.37 (s, 3H), 2.27 (m, 1H), 1.86 (m, 1H), 1.75-1.45 (m, 7H), 0.90-1.30(m, 9H); $^{13}$C NMR (300 MHz, CDCl$_3$) δ 143.2, 136.2, 129.8, 115.3, 93.9, 84.7, 55.9, 40.9, 39.5, 33.4, 26.5, 26.3, 17.6, 17.4; IR (neat) ν$_{max}$ 2923, 2851, 1450, 1153, 1095, 1033, 968.

EXAMPLE 14

Chiral Alcohol (7a)

To the chiral silyl ether 6a (1.57 g, 4.84 mmol) in 5 mL of THF was added 9-BBN (0.5 M in THF, 11.6 mL, 5.80 mmol) at −20° C. After 10 min the reaction mixture was warmed to room temperature and stirring was continued for 6 hours. TLC showed the completion of the reaction. Then 3 mL of 3 N NaOH was added and this was followed by 3 mL of 30% H$_2$O$_2$. The resulting mixture was stirred for 12 hours at room temperature and then poured into 100 mL of ether and 20 mL of saturated aqueous sodium chloride. The aqueous phase was extracted with ether and the organic solutions were combined, dried over MgSO$_4$, and concentrated. Chromatography (HE: EA=10:1) gave a colorless oil (1.43 g, 86%). $^1$H NMR (300 MHz, CDCl$_3$) 5.36, (m, 2H), 3.72 (dd, J=11.0, 3.8 Hz, 1H), 3.52 (dd, J=11.0, 5.7 Hz, 1H), 3.49 (dd, J=3.9, 6.1 Hz), 2.42-2.30 (m, 2H), 1.76-1.58 (m, 4H), 1.32-1.02 (m, 6H), 1.00 (d, J=7.1 Hz, 3H), 0.92 (s, 9H), 0.11 (s, 3H), 0.09 (s, 3H). $^{13}$C NMR (300 MHz, CDCl$_3$) 136.9, 130.3, 81.9, 65.9, 42.3, 41.1, 37.5, 33.37, 33.35, 26.5, 26.4, 18.5, 17.2, 16.7, −3.6, −3.7. IR 3398 (broad), 2957, 2927, 1254, 1074, 1024.

EXAMPLE 15

Chiral Alcohol (7b)

Chiral alcohol 7b was prepared by the procedure above from chiral olefin 6b. $^1$H NMR (400 MHz, CDCl$_3$) δ 5.36 (m, 2H), 4.65 (d, J=6.6 Hz, 1H), 4.59 (d, J=6.6 Hz, 1H), 3.82, (m, 1H), 3.49 (m, 1H), 3.41 (s, 3H), 3.34 (dd, J=7.5, 4.2 Hz, 1H), 2.82 (dd, J=7.3, 5.7 Hz, 1H), 2.37 (m, 1H), 1.95-1.80 (m, 2H), 1.78-1.60 (m, 5H), 1.32-1.00 (m, 4H), 0.98 (d, J=3.7 Hz, 3H), 0.97 (d, J=3.7 Hz, 3H); $^{13}$C NMR (400 MHz, CDCl$_3$) δ 136.5, 131.0, 99.0, 87.1, 65.4, 56.5, 40.9, 39.3, 37.4, 33.33, 33.27, 26.4, 26.3, 15.3, 14.5; IR (neat) ν$_{max}$ 3420(broad), 2922, 2850, 1449, 1147, 1095, 1032.

EXAMPLE 16

Chiral Aldehyde (8a)

To a stirred mixture of chiral alcohol 7a (220 mg, 0.64 mmol) and powdered molecular sieves 4A (600 mg) in 10 mL of methylene chloride was added 4-methylmorpholine N-oxide (NMO) (226 mg, 1.93 mmol) followed by tetra-propylammonium perruthenate (TPAP) (15.8 mg, 44.9 μmmol). After stirring at room temperature for 30 min, the mixture was filtered through a silica gel column (HE: EA=10:1), which gave chiral aldehyde 8a (215 mg, 98%) as a colorless oil. $^1$H NMR (300 MHz, CDCl$_3$) 9.69 (d, J=1.9 Hz, 1H), 5.39 (dd, J=15.4, 6.0 Hz, 1H), 5.16 (ddd, J=15.4, 8.0, 1.1 Hz), 3.75 (dd, J=6.9, 3.3 Hz, 1H), 2.51 (m, 1H), 2.37 (m, 1H), 1.87 (m, 1H), 1.73-1.60 (m, 4H), 1.32-1.02 (m, 6H), 1.11 (d, J=6.9 Hz, 3H), 0.99 (d, J=6.9 Hz, 3H), 0.88 (s, 9H), 0.08 (s, 3H), 0.06 (s, 3H); $^{13}$C NMR (300 MHz, CDCl$_3$) 204.8, 138.5, 129.3, 78.8, 50.7, 41.9, 41.0, 33.0, 32.9, 26.5, 26.3, 26.2, 18.5, 17.6, 11.4, −3.8, −4.1. IR 2956, 2928, 2854, 1724, 1255, 1079, 1038, 852.

EXAMPLE 17

Chiral Aldehyde (8b)

Chiral aldehyde 8b was prepared by the same procedure applied to chiral alcohol 7b. $^1$H NMR (400 MHz, CDCl$_3$) δ 9.68 (d, J=1.8 Hz, 1H), 5.40 (dd, J=15.6, 6.6 Hz, 1H), 5.16 (ddd, J=15.6, 8.2, 1.3 Hz), 4.66 (d, J=7.1 Hz, 1H), 4.64 (d, J=7.0 Hz, 1H), 3.63 (dd, J=7.0, 4.4 Hz, 1H), 3.35 (s, 3H), 2.64 (m, 1H), 2.40 (m, 1H), 1.86 (m, 1H), 1.72-1.55 (m, 4H), 1.32-1.02 (m, 6H), 1.11 (d, J=7.1 Hz, 3H), 1.03 (d, J=6.8 Hz, 3H); $^{13}$C NMR (300 MHz, CDCl$_3$) δ 203.9, 138.5, 129.3, 97.7, 84.2, 56.3, 49.3, 40.9, 39.9, 33.01, 32.98, 26.4, 26.3, 16.8, 11.0; IR (neat) ν$_{max}$ 2926, 2853, 1724, 1147, 1099, 1033.

EXAMPLE 18

Chiral Acetylene (9a)

To a cooled (−78° C.) solution of dimethyl 1-diazo-phosphonoacetone (Ohira-Bestmann's reagent, 916 mg, 4.17 mmol) in 30 mL of THF was added sodium methoxide (0.5 M in THF, 9.54 mL, 4.77 mmol) dropwise via cannula. After stirring for 15 min, a solution of chiral aldehyde 8a (540 mg, 1.59 mmol) in 10 mL of THF was added via cannula. The reaction mixture was slowly warmed to room temperature over 1 hour and quenched with saturated aqueous ammonium chloride solution (10 mL). The mixture was then diluted with water (45 mL) and then extracted with ether (3×45 mL). The combined extracts were washed with brine, dried over sodium sulfate and concentrated. Chromatographed (HE: EA=50:1) afforded chiral acetylene 9a (480 mg, 90%) as colorless oil. $^1$H NMR (300 MHz, CDCl$_3$) 5.39 (dd, J=15.4, 5.8 Hz, 1H), 5.27 (dd, J=15.6, 7.6 Hz, 1H), 3.37 (dd, J=6.7, 3.6 Hz, 1H), 2.65 (m, 1H), 2.39 (m, 1H), 2.02 (dd, J=2.4, 0.80 Hz), 1.92 (m, 1H), 1.74-1.60(m, 4H), 1.32-1.02 (m, 6H), 1.17 (d, J=7.1 Hz, 3H), 0.97 (d, J=6.9 Hz, 3H), 0.91 (s, 9H), 0.07 (s, 3H), 0.06 (s, 3H). $^{13}$C NMR (300 MHz, CDCl$_3$) 136.3, 131.2, 87.2, 79.1, 70.3, 41.7, 41.0, 33.3, 33.2, 31.7, 26.6, 26.41, 26.39, 18.7, 17.9, 17.4, −3.4, −3.6. IR 3312, 2957, 2927, 2854, 1253, 1080, 860.

EXAMPLE 19

Chiral MOM-Protected Acetylene (9b)

To a cooled (−78° C.) solution of dimethyl 1-diazophosphonoacetone (Ohira-Bestmann's reagent, 461 mg, 2.40 mmol) in 10 mL of THF was added sodium methoxide (0.5 M in THF, 4.80 mL, 2.40 mmol) dropwise via cannula. After stirring for 15 min, a solution of chiral aldehyde 8b (160 mg, 0.60 mmol) in 3 mL of THF was added via cannula. The reaction mixture was allowed to slowly warmed to room temperature over 1 h and quenched with saturated aqueous ammonium chloride solution (3 mL). The mixture was then diluted with water (15 mL) and then extracted with ether (3×15 mL). The combined extracts were washed with brine, dried over sodium sulfate and concentrated. Chromatographed (HE: EA=10:1) afforded chiral acetylene 9b (136 mg, 85%) as colorless oil. $^1$H NMR (400 MHz, CDCl$_3$) δ 5.46 (dd, J=15.4, 6.6 Hz, 1H), 5.24 (ddd, J=15.4, 8.2, 1.2 Hz), 4.74 (d, J=7.0 Hz, 1H), 4.70 (d, J=7.0 Hz, 1H), 3.42 (s, 3H), 3.14, (dd, J=7.9, 3.5 Hz, 1H), 2.76 (m, 1H), 2.49 (m, 1H), 2.07 (d, J=2.6 Hz, 1H), 1.96-1.84 (m, 1H), 1.72-1.58 (m, 5H), 1.23 (d, J=6.7 Hz, 3H), 1.18-1.07 (m, 5H), 1.04 (d, J=6.8 Hz, 3H); $^{13}$C NMR (400 MHz, CDCl$_3$) δ 137.2, 130.1, 98.5, 86.3, 85.9, 70.1, 70.0, 56.5, 41.0, 40.9, 33.2, 33.1, 29.9, 26.4, 26.3, 18.6, 17.2; IR (neat) ν$_{max}$ 2926, 2.851, 1149, 1096, 1035.

EXAMPLE 20

Chiral Aldehyde (10a)

A solution of Sudan red 7B (1 mg/mL, 100 μL) was added to a solution of chiral acetylene 9a (153 mg, 0.455 mmol) in 4 mL of methylene chloride. The solution was cooled to −78° C. and flushed with argon for 5 min. A flow of ozone was passed through the solution until the pink color disappeared (ca, 5 min). The remaining ozone was then purged with argon for 10 min, and then triphenyl phosphine (119 mg, 0.455 mmol) was added. After stirring for 1 h at −78° C. and then 6 hours at ambient temperature, the solution was concentrated in vacuo. Chromatography (HE: EA=40:1) gave a colorless oil (101 mg, 86%). $^1$H NMR (300 MHz, CDCl$_3$) 9.89 (d, J=0.90 Hz, 1H), 4.08 (m, 1H), 2.76-2.60 (m, 2H), 2.10 (d, J=2.7 Hz, 1H), 1.22 (d, J=7.1 Hz, 3H), 1.12 (d, J=7.1 Hz, 3H), 0.90 (s, 9H), 0.11 (s, 3H), 0.06 (s, 3H). $^{13}$C NMR (300 MHz, CDCl$_3$) 204.3, 74.1, 72.1, 50.8, 31.4, 26.1, 18.5, 17.3, 9.8, −4.0, −4.1. IR 3312, 2955, 2932, 2886, 1711, 1463, 1120, 837, 776.

EXAMPLE 21

Chiral Aldehyde (10b)

A solution of Sudan red 7B (1 mg/mL, 100 μL) is added to a solution of acetylene 9b in methylene chloride. The solution is cooled to −78° C. and flushed with argon for 5 min. A flow of ozone is passed through the solution until the pink color disappears (ca, 5 min). The remaining ozone is then purged with argon for 10 min, and then triphenyl phosphine is added. After stirring for 1 h at −78° C. and then 6 hours at ambient temperature, the solution is concentrated in vacuo. Chromatography (HE: EA=40:1) gives aldehyde 10b.

EXAMPLE 22

Chiral Vinyl Iodide (1d)

A suspension of ethyl triphenyl phosphine iodide (4.57 g, 10.9 mmol) in 45 mL of THF at room temperature was treated with n-BuLi (2.5 M in hexanes, 4.44 mL, 11.1 mmol). After 10 min, all solid disappeared. The resulting red transparent solution was added to a cold solution (−78° C.) of iodine (2.64 g, 10.4 mmol in 70 mL of THF). After 10 min at −78° C., the reaction mixture was warmed to room temperature over 2 hours. The yellow slurry was filtered and washed with hexanes to give 6.0 g solid.

To a suspension of the solid prepared above (385 mg, 0.708 mmol) in 3 mL of THF at −25° C., sodium hexamethyldisilazane (NaHMDS) (1.0 M in THF, 0.708 mL, 0.708 mmol) was added dropwise. After 15 min, the resulting red solution was cooled to −35° C. Aldehyde 10 (80 mg, 0.315 mmol) in 1 mL of THF was added dropwise. The reaction mixture was stirred for 45 min at −35° C. and then warmed to room temperature over 2 hours. The reaction was then quenched with methanol (0.5 mL) and concentrated. The residue was filtered through a silica column (50% ethyl acetate in hexanes) and purified by chromatography (HE: EA=50:1) to give chiral vinyl iodide 1d as colorless oil (49 mg, 41%). $^1$HNMR (300 MHz, CDCl$_3$) 5.41 (dq, J=8.9, 1.4 Hz, 1H), 3.61 (dd, J=5.8, 4.7 Hz, 1H), 2.70-2.58 (m, 2H), 2.47 (d, J=1.4 Hz, 3H), 2.07 (d, J=2.5 Hz, 1H), 1.21 (d, J=7.1 Hz, 3H), 0.98 (d, J=6.9 Hz, 3H), 0.92 (s, 9H), 0.09 (s, 3H), 0.05 (s, 3H). $^{13}$C NMR (300 MHz, CDCl$_3$) 139.2, 99.7, 87.3, 77.5, 70.6, 45.4, 33.9, 32.1, 26.3, 18.6, 17.3, 15.2, −3.6, −3.7. IR 3311, 2894, 2885, 2856, 1471, 1461, 1252, 1112.

EXAMPLE 23

Chiral Vinyl Iodide (1e)

To a suspension of the iodinated Wittig reagent prepared as above in THF at −25° C., sodium hexamethyldisilazane (NaHMDS, 1 equiv) is added dropwise. After 15 min, the resulting red solution is cooled to −35° C. Aldehyde 10 (0.5 equiv) in 1 mL of THF is added dropwise. The reaction mixture is stirred for 45 min at −35° C. and then warmed to room temperature over 2 hours. Quenching with methanol and concentration gives a residue that is filtered through a silica column (50% ethyl acetate in hexanes) and purified by chromatography to give chiral vinyl iodide 1e.

Synthesis of Aldehyde 13 (Scheme 2)

EXAMPLE 24

Chiral Alcohol (11)

To the solution of (−)-B-methoxydiisopinocampheylborane (215 mg, 0.680 mmol) in 5 mL of ether was added allyl magnesium bromide (1.0 M in ether, 649 μL, 649 mmol) dropwise at room temperature. After 1 h at room temperature, the reaction mixture was cooled to −78° C. Chiral aldehyde 8a (210 mg, 0.618 mmol) in 2 mL of ether was added dropwise. After being stirred for 5 h at −78° C. and 5 h at −40° C., the reaction was added 1 mL of 3N NaOH and 1 mL of 30% $H_2O_2$ and warmed to room temperature. The mixture was refluxed 2 h and then poured into brine (10 mL). The aqueous phase was extracted with ether and the organic phase was combined, dried ($MgSO_4$), and concentrated. Chromatography (HE: $CH_2Cl_2$=1:1) first gave chiral alcohol 11 (168 mg, 71%) as a colorless oil and then the 4R isomer (40.1 mg, 17%) as a colorless oil.

For chiral alcohol 11: $^1H$ NMR (300 MHz, $CDCl_3$) δ 5.90 (m, 1H), 5.30 (m, 2H), 5.11 (m, 1H), 5.07 (d, J=1.5 Hz, 1H), 3.64 (tt, J=8.5, 2.7 Hz, 1H), 3.53 (dd, J=6.0, 4.6 Hz, 1H), 2.93 (d, J=2.5 Hz, 1H), 2.42-2.28 (m, 2H), 2.14-2.02 (m, 1H), 1.98-1.60 (m, 7H), 1.38-1.01, (m, 5H), 0.97 (d, J=6.9 Hz, 1H), 0.92 (s, 9H), 0.85 (d, J=6.9 Hz, 1H), 0.09 (s, 3H), 0.08 (s, 3H). $^{13}C$ NMR (300 MHz, $CDCl_3$) δ 137.0, 135.8, 131.0, 117.3, 80.9, 72.8, 42.8, 42.1, 41.0, 39.0, 33.41, 33.34, 26.5, 26.38, 26.35, 18.5, 17.1, 15.3, −3.7, −3.8; IR (neat) $v_{max}$ 3500 (broad), 2926, 2854, 1462, 1449, 1254, 1003, 974, 835. For the 4R isomer of chiral alcohol 11. $^1H$ NMR (300 MHz, $CDCl_3$) δ 5.76 (m, 1H), 5.31 (m, 2H), 5.12-4.98 (m, 2H), 4.20 (t, J=6.7 Hz, 1H), 3.52 (dd, J=7.7, 2.2 Hz, 1H), 3.45 (s, 1H), 2.47 (m, 1H), 2.28 (m, 1H), 2.03 (m, 1H), 1.98-1.60 (m, 7H), 1.38-1.01, (m, 5H), 1.01 (d, J=6.9 Hz, 3H), 0.98 (d, J=6.9 Hz, 3H), 0.92 (s, 9H), 0.13 (s, 3H), 0.11 (s, 3H). $^{13}C$ NMR (300 MHz, $CDCl_3$) δ 136.8, 135.9, 130.1, 116.9, 83.8, 70.5, 42.0, 41.1, 39.6, 37.2, 33.38, 33.32, 26.5, 26.4, 18.6, 12.3, −3.3, −3.6; IR (neat) $v_{max}$ 3505 (broad), 2926, 2854, 1462, 1449, 1255, 1084, 1019, 1003.

EXAMPLE 25

Chiral Aldehyde (12)

To chiral alcohol 11 (191 mg, 0.50 mmol) in 15 mL of $CH_2Cl_2$ at −78° C., O3 was flushed in until the solution turned into blue. After the solution being flushed with argon for 10 min at −78° C., $Ph_3P$ (327 mg, 1.25 mmol) was added. After 1 h at −78° C. and 6 h at room temperature, the mixture was concentrated. Chromatography (HE: EA=5:1) gave chiral compound 12 as a colorless oil (125 mg, 91%). $^1H$ NMR (300 MHz, $CDCl_3$) δ 9.82 (m, 1H), 5.48 (d, J=10.7 Hz, 0.5H), 5.22 (s, 0.5H), 4.83 (d, J=10.4, 0.5H), 4.38 (m, 0.5H), 4.08 (m, 0.5H), 3.74 (s, 0.5H), 3.66 (t, J=2.5 Hz, 0.5H), 2.65-2.40 (m, 2H), 2.10-1.62 (m, 2H), 1.03-0.79 (m, 15H), 0.14 (s, 1.5H), 0.10 (s, 1.5H), 0.06 (s, 1.5H), 0.04 (s, 1.5H); IR (neat) $v_{max}$ 3450 (broad), 2962, 2930, 1724, 1708, 1172, 1154, 1109, 1095.

EXAMPLE 26

Acetal (13)

To a solution of chiral compound 12 (120 mg, 0.438 mmol) in 1 mL of $CH_2Cl_2$ was added imidazole (44.7 mg, 0.657 mmol), DMAP (13.4 mg, 0.11 mmol), TBDMSCl(198 mg, 1.31 mmol) at 0° C. The mixture was stirred for 12 h and then directly loaded on silica gel column. Chromatography (HE: EA=10:1) gave compound 13 as a colorless oil (128 mg, 70%). $^1H$ NMR (300 MHz, $CDCl_3$) δ 9.82 (t, J=2.7 Hz, 1H), 5.21 (d, J=3.0 Hz, 1H), 4.05 (dt, J=10.2, 6.3 Hz, 1H), 3.66 (t, J=2.7 Hz, 1H), 2.49 (m, 2H), 1.88-1.77 (m, 1H), 1.76-1.64 (m, 1H), 0.94 (d, J=7.2 Hz, 3H), 0.92 (s, 9H), 0.88 (s, 9H), 0.80 (d, J=7.0 Hz, 3H), 0.07 (s, 3H), 0.06 (s, 6H), 0.05 (s, 3H); $^{13}C$ NMR (300 MHz, $CDCl_3$) δ 202.5, 94.6, 76.6, 72.2, 46.9, 43.0, 34.8, 26.1, 26.0, 18.3, 13.8, 9.60, −3.9, −4.3, −4.7, −5.1; IR (neat) $v_{max}$ 2955, 2928, 1731, 1462, 1174, 1120, 1049, 836.

Synthesis of (+)-Discodermolide (Scheme 3)

EXAMPLE 27

Alcohol (14)

To a cold solution (−78° C.) of alkyne 1e is added dropwise 1 equivalent of LDA in cyclohexane. The mixture is stirred at −78° C. over 1 h. Aldehyde 13 is added dropwise in THF. The temperature is increased to −40° C. and stirred for 1 h. Water is added dropwise at −40° C. and the mixture is warmed to room temperature. The aqueous phase is extracted with ether and organic phases are combined, dried ($Na_2SO_4$). Chromatography (HE: EA=mixtures) gives compound 14.

EXAMPLE 28

MOM Ether (15)

To a solution of alcohol 14 in methylene chloride at 0° C. is added MOMCl (approx 4 equiv), $^iPr_2NEt$ (approx 8 equiv) and DMAP (approx 4 equiv). The reaction is stirred for 2 h at 0° C. and then 16 h at room temperature. A saturated solution of sodium carbonate is added to quench the reaction. The aqueous phase is extracted with methylene chloride and the organic phases are combined, dried ($MgSO_4$), and concentrated. Chromatography (HE: EA mixtures) gives the MOM ether 15.

EXAMPLE 29

Suzuki Product (17)

A 1.0 M solution of anhydrous $ZnCl_2$ (1.2 equiv) is added to a solution of iodide 16 (1.2 equiv) in ether and the resulting solution is then cooled to −78° C. Then t-BuLi (1.0 equiv) is added dropwise. The resulting solution is stirred for 5 min and then warmed to room temperature. After stirring for 1 h, the resulting suspension is transferred by cannula into a mixture of vinyl iodide 15 (1.0 equiv) and $Pd(PPh_3)_4$ (0.12 equiv). The reaction mixture is stirred overnight in the absence of light and quenched with water. The mixture is diluted ether and the layers are separated. The water layer is extracted and the combined organic layers are washed with saturated aqueous $NaHCO_3$ and brine, dried ($MgSO_4$), filtered and concentrated. Chromatography (HE: EA mixtures) gives compound 17.

EXAMPLE 30

Diene (18)

To a solution of compound 17 in 5 mL of hexanes is added Lindlar catalyst (Pd/$CaCO_3$ poisoned with Pb, 5% Pd, 50 mg) and quinoline (5 μL). $H_2$ is bubbled through the reaction mixture for 20 min and the resultant suspension is stirred vigorously for 24 h under a balloon atmosphere of $H_2$. After filtration through Celite with ether, the solution is concentrated. Chromatography (HE: EA mixtures) gives compound 18.

EXAMPLE 31

Alcohol (19)

To a solution of compound 18 (1 equiv) in $CH_2Cl_2$ is added DIBAL (3 equiv) at 0° C. The resulting solution is stirred for 5 h and quenched with pH 7.0 buffer (0.1 mL), then diluted with $CH_2Cl_2$ (10 mL). To the mixture is then added 2 mL of saturated sodium potassium tartrate solution and it was extracted with $CH_2Cl_2$. The organic layer is washed with water, dried and concentrated. Chromatography (HE: EA mixtures) gives compound 19.

EXAMPLE 32

Aldehyde (20)

To a solution of compound 19 in $CH_2Cl_2$ are added Dess-Martin periodinane (1.1 equiv) and $NaHCO_3$ (3 equiv). The resulting solution is stirred for 3 h and quenched with equal volumes of saturated $NaS_2O_3$ solution and saturated $NaHCO_3$. The mixture is then extracted with ether. The organic solution is then washed with water, dried and concentrated. The resulting residue is used without purification.

EXAMPLE 33

Tetraene (21)

To a −78° C. solution of freshly distilled allyldiphenylphosphine in THF (2 mL) is added t-butyllithium (1.0 equiv) and stirred for 5 min. The solution is warmed to 0° C., stirred for 30 min and cooled to −78° C. The solution is treated with freshly distilled $Ti(Oi-Pr)_4$ (1.0 equiv) and stirred for 30 min. A precooled (−78° C.) solution of aldehyde 10 (0.5 equi) in THF is added via cannula and stirred for 1 h, then warmed to 0° C. Iodomethane (5 equiv) is added, and the solution is warmed to room temperature and stirred for 16 h. The solution is quenched with pH 7.0 buffer and extracted with $CH_2Cl_2$ and ether. The combined organic layers are washed with brine solution, dried and concentrated. Chromatography (HE: EA=2:1) gives tetraene 21.

EXAMPLE 34

Alcohol (22)

At 0° C., a solution of 1 equivalent tetraene 21 in $CH_2Cl_2$ (3 mL) is treated with $H_2O$ (50 μL) and 1.2 equivalents DDQ. The mixture is stirred for 10 min at 0° C., warmed to rt and stirred an additional 5 min. The mixture is quenched with 0.5 mL saturated $NaHCO_3$, diluted with $CH_2Cl_2$ (30 mL), and washed with water (50 mL) and saturated brine (50 mL). The combined organic layers are dried and concentrated. Chromatography (HE: EA=2:1) gives compound 22.

EXAMPLE 35

Urethane (23)

A solution of alcohol 22 in $CH_2Cl_2$ is treated with $ClCCON=C=O$ (1.2 equiv) at room temperature for 30 min. The solution is loaded directly onto neutral $Al_2O_3$. After 4 h, the material is flushed from the $Al_2O_3$ (EtOAc) and the eluent is concentrated. Chromatography (HE: EA=10:1) gives compound 23.

EXAMPLE 36

Lactol (24)

A solution of compound 23 in THF is treated with excess TBAF (1.0 M in THF, 1 mL) at room temperature for 30 min. The organic layer is separated and the aqueous layer is extracted with ether. The combined organic layer is combined, dried and concentrated. Chromatography (HE: EA=2:1) gives compound 24.

EXAMPLE 37

Lactone (25)

A solution of compound 24 in $CH_2Cl_2$ is added $MnO_2$ (3 mole equiv). The mixture is stirred for 12 h at room temperature and then concentrated. The resulting residue is loaded on silica gel. Elution gives compound 25.

EXAMPLE 38

(+)-Discodermolide

To a solution of compound 25 in THF is added an aqueous solution of 4 N HCl. The mixture is stirred at room temperature for 24 h. Saturated aqueous $NaHCO_3$ is added dropwise followed by EtOAc. The organic phase is washed with brine. The aqueous phase is extracted with EtOAc, and the combined extracts are dried and concentrated. Chromatography (HE: EA=2:1) gives a white solid.

Thus, whereas there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

We claim:

1. A compound having the formula:

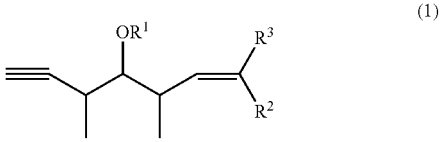

(1)

wherein R' is H or a protecting group, and R2 and R3 each independently represent H, methyl, or a leaving group, provided that at least one of R2 and R3 is a leaving group.

2. A compound according to claim 1, wherein only one of R2 and R3 is a leaving group.

3. A compound according to claim 1, wherein R' is a protecting group.

4. A compound according to claim 3, wherein the protecting group is a member of the silyl class of protecting groups.

5. A compound according to claim 4, wherein the protecting group has the formula:

$$-Si(O_xR^4)(O_yR^5)(O_zR^{6\sim}) \quad (2)$$

wherein x, y, and z independently represent 0 or 1; and
R4, R5 and R~~ each independently represent a linear or branched alkyl group having one to four carbon atoms, any two of the alkyl groups optionally being connected to form a silicon-containing ring; or an aryl group selected from the group consisting of phenyl, pyridinyl, pyrrolyl, and furanyl.

6. A compound according to claim 5, wherein x, y, and z are all 0, and the silyl group is selected from triethylsilyl, tri-(n-propyl)silyl, triisopropylsilyl, tri-(n-butyl)silyl, tri-isobutylsilyl, t-butyldimethylsilyl, t-butyldiphenylsilyl, phenyldimethylsilyl, methyldiphenylsilyl, or triphenylsilyl.

7. A compound according to claim 5, wherein at least one of x, y, and z is 1, and the silyl group is selected from trimethoxysilyl, dimethoxymethylsilyl, methoxydimethylsilyl, ethoxydimethylsilyl, methoxydiethylsilyl, isopropoxydimethylsilyl, phenoxydimethylsilyl, phenoxydiethylsilyl, methyldiphenoxysilyl, [2,4,6-tri-(t-butyl)phenoxy]dimethylsilyl, t-butoxydimethylsilyl, tbutoxydiphenylsilyl, (t-butyl)(methoxy)phenylsilyl, and methoxydiphenylsilyl.

8. A compound according to claim 4, wherein the protecting group is tbutyldimethylsilyl.

9. A compound according to claim 3, wherein the protecting group is a member of the acetal/ketal class of protecting groups.

10. A compound according to claim 9, wherein the protecting group has the formula:

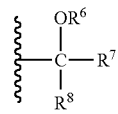

wherein:
R~ represents an alkyl group optionally substituted with an aryl group; R7 represents hydrogen, an alkyl group, or an aryl group; and R8 represents hydrogen or an alkyl group;
the alkyl groups of R~R7, and R8 are linear or branched, having one to four carbon atoms, the alkyl groups of R6 and R7 optionally being joined to form a five or six member saturated ring;
the aryl substituent of R6 and the aryl group of R7 are phenyl, pyridinyl, pyrrolyl, or furanyl.

11. A compound according to claim 10, wherein the acetal/ketal protecting groups are selected from the group consisting of methoxymethyl, ethoxymethyl, tetrahydropyranyl, and benzyloxymethyl.

12. A compound according to claim 10, wherein the acetal/ketal protecting group is methoxymethyl.

13. A compound according to claim 9, wherein the acetal/ketal protecting groups are selected from the group consisting of p-methoxybenzyloxymethyl and betatrimethylsilyloxyethoxymethyl groups.

14. A compound according to claim 2, wherein the protecting group is a member of the class of arylmethyl protecting groups, wherein the aryl group is phenyl, pyridinyl, pyrrolyl, or furanyl, optionally substituted with methoxy, ethoxy, nitro, or halo.

15. A compound according to claim 14, wherein the protecting group is selected from the group consisting of benzyl, p-methoxybenzyl, and p-ethoxybenzyl.

16. A compound according to claim 15, wherein the protecting group is pmethoxybenzyl.

17. A compound according to claim 2, wherein R2 is a leaving group and R3 is a methyl group.

18. A compound according to claim 17, wherein R2 is C1.

19. A compound according to claim 17, wherein R2 is Br.

20. A compound according to claim 17, wherein R2 is I.

21. A compound according to claim 17, wherein R2 is a sulfonate ester group.

22. A compound according to claim 21, wherein the sulfonate ester group is selected from triflate, mesylate, benzensulfonate and tosylate.

23. A compound according to claim 17, wherein R2 is a phosphate ester group.

24. A compound according to claim 20, wherein R3 is methyl.

25. A compound according to claim 20, wherein R3 is H.

26. A compound according to claim 1, having the formula:

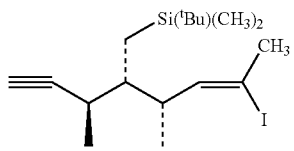

27. A compound according to claim 1, having the formula:

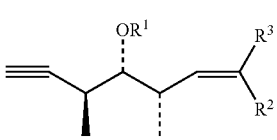

wherein R' is H or a protecting group, R2 and R3 each independently represent H, methyl, or a leaving group, provided that at least one, but not both, of R2 and R3 is a leaving group.

* * * * *